United States Patent [19]

Hara et al.

[11] Patent Number: 5,807,711
[45] Date of Patent: Sep. 15, 1998

[54] PARENCHYMAL HEPATOCYTE GROWTH FACTORS

[75] Inventors: Hiroshi Hara; Hiromitsu Yoshimura; Yumiko Matsuki; Saeko Shindo; Kazunori Hanada, all of Tokyo, Japan

[73] Assignee: Taisho Pharmaceutical Co., Ltd., Tokyo, Japan

[21] Appl. No.: 525,505

[22] PCT Filed: Mar. 22, 1994

[86] PCT No.: PCT/JP94/00455

§ 371 Date: Sep. 22, 1995

§ 102(e) Date: Sep. 22, 1995

[87] PCT Pub. No.: WO94/21678

PCT Pub. Date: Sep. 29, 1994

[30] Foreign Application Priority Data

Mar. 23, 1993 [JP] Japan ................................ 5-063905

[51] Int. Cl.⁶ .......................... C07K 1/32; C07K 14/475; C12N 5/10; C12N 15/18
[52] U.S. Cl. ..................... 435/69.4; 435/243; 435/320.1; 435/325; 530/399; 530/413; 536/23.51
[58] Field of Search ..................... 530/350, 399, 530/413; 435/69.1, 69.4, 70.1, 240.1, 320.1, 243, 325; 536/23.1, 23.5, 23.51

[56] References Cited

U.S. PATENT DOCUMENTS 4,960,700  10/1990  Malfroy-Camine et al. ......... 435/172.3
5,155,218  10/1992  Weinshank et al. ..................... 536/27

FOREIGN PATENT DOCUMENTS 0 412 557   2/1991   European Pat. Off. .

OTHER PUBLICATIONS

Database WPI, Section Ch, Week 9201, Derwent Publications Ltd., Class B04, AN 92–002670, "Recombinant Rat Liver Parenchymatous Cell Growth Factor Providing Means for Growth of Liver Parenchymatous Cell Outside of Living Body", JP 03 255 096 A (Toyobo KK), 13 Nov. 1991.

Yamamoto et al. Biochem. Biophys. Res. Comm. 193(2): 681–687, 1993.

*Primary Examiner*—John Ulm
*Assistant Examiner*—Christine Saoud
*Attorney, Agent, or Firm*—Oblon, Spivak, McClelland, Maier & Neustadt, P.C.

[57]           ABSTRACT

A novel parenchymal hepatocyte growth factor originating in a human or animal liver, having an estimated molecular weight according to nonreductive SDS-PAGE of about 63,000 to about 69,000, an estimated molecular weight according to reductive SDS-PAGE of about 32,000 to about 36,000 and an estimated molecular weight according to gel filtration of about 60 to about 70 Kd; and having an activity of effecting the growth of parenchymal hepatocyte has been obtained from the hemihepatectomized tissue. Furthermore, a gene coding for the above substance has been obtained from the mRNA of the above tissue and it has thus become possible to mass-produce the above substance.

11 Claims, 7 Drawing Sheets

```
              1        10        20        30        40        50        60        70
RAT-DERIVED   MGEIRSFVLITVALILGKESWVLGDENCLQEQVRLRAQVRQLETRVKQQQVVIAQLLHEKEVQFLDRGQE
              | || | ||| | |  | | ||| |||||||| ||||||||||| ||| | ||||||| ||
HUMAN-DERIVED MAKVFSFILVTTALIMGREISALED--CAQEQMRLRAQVRLLETRVKQQQVKIKQLLQENEVQFLDKGDE
              1        10        20        30        40        50        60

80        90       100       110       120       130       140
              DSFIDLGGKRHYADCSEIYNDGFKHSGFYKIKPLQSLAEFSVYCDMSDGGGWTVIQRRSDGSENFNRGWN
              |||| || ||||||||| |||  | |||||||||||||||||||||||||||||||||||||||||||
              NTVVDLGSKRQYADCSEIFNDGYKLSGFYKIKPLQSPAEFSVYCDMSDGGGWTVIQRRSDGSENFNRGWK
                      70        80        90       100       110       120       130

150       160       170       180       190       200       210
              DYENGFGNFVQSNGEYWLGNKNINLLTMQGDYTLKIDLTDFEKNSRFAQYEKFKVGDEKSFYELNIGEYS
              |||||||||||   |||||||||  |  |||||||||| ||||||| ||||  |||||| |||||||||
              DYENGFGNFVQKHGEYWLGNKNLHFLTTQEDYTLKIDLADFEKNSRYAQYKNFKVGDEKNFYELNIGEYS
                      150       160       170       180       190       200

220       230       240       250       260       270       280
              GTAGDSLSGTFHPEVQMWASHQTMKFSTRDRDNDNYNGNCAEEEQSGWWFNRCHSANLNGVYYQGPYRAE
              ||||||| | |||||||||||| |||||| || ||| |||||| ||||||||||||||||||||  |||  |
              GTAGDSLAGNFHPEVQMWASHQRMKFSTWDRDHDNYEGNCAEEDQSGWWFNRCHSANLNGVYYSGPYTAK
                      220       230       240       250       260       270

290       300       310
              TDNGVVWYTWRGWWYSLKSVVMKIRPSDFIPNIV.
              ||||  ||||| |||||||||||||| ||||||
              TDNGIVWYTWHGWWYSLKSVVMKIRPNDFIPNVI.
                      290       300       310
```

FIG.1

```
                  10        20        30        40        50        60
RAT-DERIVED   GACCCAGCCTAGCTGAGTA-CTGATTCATTT-TGATGTGAGT---------GGGAAGAATGGGGGAGATT
                 |||||| || |||| ||| || ||| | |||         ||| | |||| ||  |
HUMAN-DERIVED    TGAGCTGGGTCTCTGACTCACTTCTGACTTTAGTTTTTTCAAGGGGGAACATGGCAAAGGTG
                 X        10        20        30        40        50        60

70        80        90       100       110       120        130
CGCAGCTTTGTCCTCATCACTGTTGCTCTGATTCTGGGCAAGGAGAGCTGGGTCCTCGGAGATGAGAACT
||| || ||||   | ||   |||||||| |||||| ||| | ||| ||||            || |||
TTCAGTTTCATCCTTGTTACCACCGCTCTGATAATGGGCAGGGAAATTTCGGCGCTCG------AGGACT
      70        80        90       100       110        120

140       150       160       170       180       190       200
GTTTGCAGGAGCAGGTCAGGCTCAGGGCTCAGGTGCGCCAGCTTGAGACCCGGGTCAAACAACAACAGGT
|||  ||||||||| |   |||||||| || ||||||| ||| |||||||||||||||||||| |||||||
GTGCCCAGGAGCAGATGCGGCTCAGAGCCCAGGTGCGCCTGCTTGAGACCCGGGTCAAACAGCAACAGGT
    130       140       150       160       170       180       190

210       220       230       240       250       260       270
GGTGATTGCACAGCTCTTGCACGAGAAGGAGGTCCAGTTCCTGGATAGAGGACAGGAGGACAGCTTCATT
|||     ||||| ||||| ||||| || |||||||||||| |||| | ||| | || ||
CAAGATCAAGCAGCTTTTGCAGGAGAATGAAGTCCAGTTCCTTGATAAAGGAGATGAGAATACTGTCGTT
       200       210       220       230       240       250       260

280       290       300       310       320       330       340
GACCTTGGAGGCAAGAGGCATTACGCAGATTGTTCAGAGATTTACAATGATGGATTTAAACATAGTGGGT
|| |||||| |||||||||||| ||||||||||||||||||||||| |||||||||| | ||||| |||| |
GATCTTGGAAGCAAGAGGCAGTATGCAGATTGTTCAGAGATTTTCAATGATGGGTATAAGCTCAGTGGAT
       270       280       290       300       310       320       330

350       360       370       380       390       400       410
TTTACAAAATCAAACCTCTTCAGAGTCTGGCAGAATTCTCTGTTTATTGTGATATGTCTGATGGAGGAGG
||||||||||||||||||| |||||| | ||||||||||| ||||||||||||||| |||||||||||||||
TTTACAAAATCAAACCTCTCCAGAGCCCAGCAGAATTTTCTGTTTATTGTGACATGTCCGATGGAGGAGG
       340       350       360       370       380       390       400

420       430       440       450       460       470       480
ATGGACTGTAATTCAGAGACCGATCTGACGGCAGTGAGAACTTTAACAGGGGTTGGAACGACTATGAAAAT
|||||||||||||||||||||||||||  |||||||| | ||||||||||| || |||| ||||||||||||
ATGGACTGTAATTCAGAGACGATCTGATGGCAGTGAAAACTTTAACAGAGGATGGAAAGACTATGAAAAT
       410       420       430       440       450       460       470

490       500       510       520       530       540       550
GGCTTTGGAAACTTTGTCCAAAGCAATGGTGAATACTGGCTGGGTAACAAAAACATTAACTTGCTGACTA
||||||||||| |||||||||  ||||||||||| |  ||||||| |||||  |||||  | ||| |||| |
GGCTTTGGAAATTTTGTCCAAAAACATGGTGAATATTGGCTGGGCAATAAAAATCTTCACTTCTTGACCA
      480       490       500       510       520       530       540
```

FIG.2

```
              560       570       580       590       600       610       620
RAT-DERIVED   TGCAAGGAGACTACACTTTAAAAATCGACCTGACAGACTTTGAGAAAAACAGCCGCTTCGCACAATACGA
              ||||  |||||||||||||||||||||||| ||||  ||||| |||||  |||||  |  ||||||||  |
HUMAN-DERIVED CTCAAGAAGACTACACTTTAAAAATCGACCTTGCAGATTTTGAAAAAAATAGCCGTTATGCACAATATAA
              550       560       570       580       590       600       610

630       640       650       660       670       680       690
              AAAATTTAAAGTTGGCGATGAAAAGTCTTTTTACGAACTGAATATTGGAGAATATTCTGGCACCGCCGGA
              || || |||||||||| ||||||| |||  |||  |||||  |||||||||| ||||||||||| || |||
              GAATTTCAAAGTTGGAGATGAAAAGAATTTCTACGAGTTGAATATTGGGGAATATTCTGGAACAGCTGGA
              620       630       640       650       660       670       680

700       710       720       730       740       750       760
              GACTCCCTGTCGGGAACATTTCACCCTGAAGTGCAGTGGTGGGCTAGTCACCAAACAATGAAGTTCAGCA
              || ||||| ||||  | |||||  |||||  ||||||||||||||||||||||||  ||||||| ||||||
              GATTCCCTTGCGGGGAATTTTCATCCTGAGGTGCAGTGGTGGGCTAGTCACCAAAGAATGAAATTCAGCA
              690       700       710       720       730       740       750

770       780       790       800       810       820       830
              CACGGGACAGAGACAACGACAACTACAACGGGAACTGTGCTGAGGAGGAACAGTCTGGCTGGTGGTTTAA
              |  ||||||||   |||||||||  |  ||||||| || || || || ||||||||||||||||||||||
              CGTGGGACAGAGATCATGACAACTATGAAGGGAACTGCGCAGAAGAAGATCAGTCTGGCTGGTGGTTTAA
              760       770       780       790       800       810       820

840       850       860       870       880       890       900
              CAGGTGTCACTCTGCAAACCTGAACGGCGTGTACTACCAAGGTCCCTACAGAGCAGAAACCGATAATGGT
              ||||||||||||||||||||||||| || || |||||||   || ||||||| ||  |||| || |||||
              CAGGTGTCACTCTGCAAACCTGAATGGTGTATACTACAGCGGCCCCTACACGGCTAAAACAGACAATGGG
              830       840       850       860       870       880       890

910       920       930       940       950       960       970
              GTTGTCTGGTACACCTGGCGTGGGTGGTGGTATTCCTTGAAATCTGTGGTTATGAAAATTAGGCCCAGTG
              |||||||||||||||||||| ||||||||||||| |||||||||||||||||||||||||||||| | ||
              ATTGTCTGGTACACCTGGCATGGGTGGTGGTATTCTCTGAAATCTGTGGTTATGAAAATTAGGCCAAATG
              900       910       920       930       940       950       960

980       990       1000      1010      1020      1030      1040
              ATTTTATTCCAAATATCGTTTAGTTGTCCCA-TTGGGATCTGCTTTCTGTGATTCATCTTGGTTTTTAAA
              |||||||||||||||  |  |||| |||  |  | ||||| |  ||||||  |||||| ||||  |||| |
              ATTTTATTCCAAATGTAATTTAATTGCTGCTGTTGGGCTTTCGTTTCTGCAATTCAGCTTTGTTTAAAGT
              970       980       990       1000      1010      1020      1030

1050      1060      1070      1080      1090      1100      X
              TGTTTGAAAAAAATATACA-ATTCTGAATA-ATACACTCGTGGCCATGGTGAAAAAAAAAAAAAAA
              |||||||||         |||   ||||||||| || ||   || || |||  ||
              GATTTGAAAAA        TACTCATTCTGAACATATCCAGC        GCAATCATGATAACTGTTGTGAG
              1040      1050      1060      1070                1080      1090
```

FIG.3

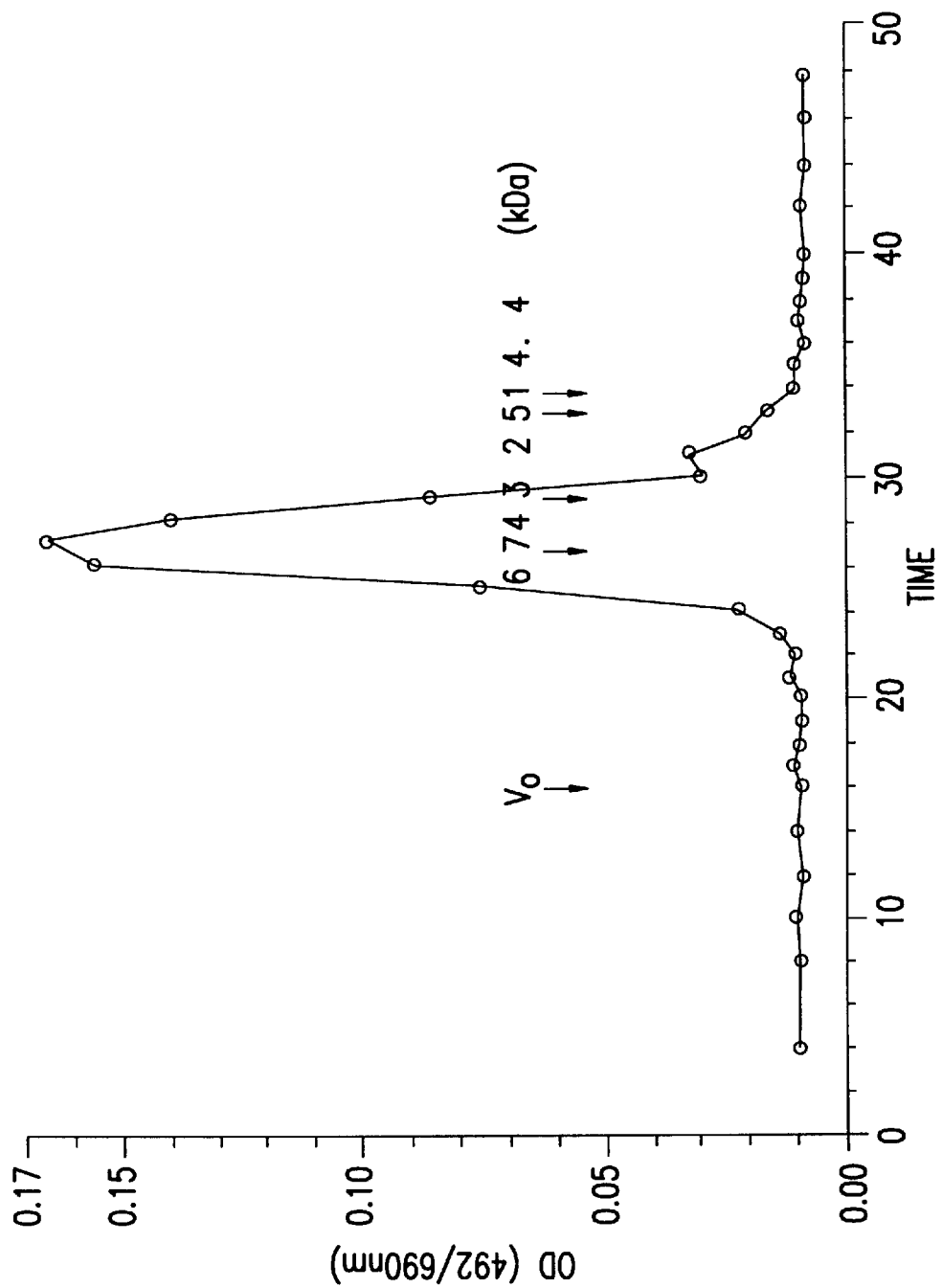

PARENCHYMAL HEPATOCYTE GROWTH FACTORS

TECHNICAL FIELD

The present invention relates to a parenchymal hepatocyte growth substance originating in a human or animal liver and having an activity of effecting the extracellular growth of parenchymal hepatocytes, and a gene coding for the above substance.

More particularly, the present invention relates to a parenchymal hepatocyte growth substance originating in a human or animal liver which is expected to be effective for the treatment of liver diseases through the improvement of liver functions by proliferating normal hepatocytes in many liver diseases including hepatitis, liver cirrhosis and hepatoma, as well as a gene coding for the said substance.

BACKGROUND ART

It has been reported from old that when the liver suffers from various damages, regeneration of the liver occurs. The first report that partial hepatectomy of rat liver caused liver regeneration was made by Higgins, G. M., et al. in Arch. Pathol., 12, 186–202 (1931).

A hepatocyte growth factor (HGF) from rat platelets was found as a substance for promoting the growth of liver cells by Toshikazu Nakamura et al., see Biochem. Biophys. Res. Commun., 122, 1450–1459 (1984).

Likewise human HGF (hHGF) originating in human blood was discovered by Aida et al., see Japanese Patent Application KOKAI No. 63-22526.

However, recent studies reveal that these substances (factors) are one of cytokines produced in many organs (lung, liver, kidney, spleen, etc.) of rat and human and also exhibit the activities of accelerating infiltration of human cancer cells (renal tubule MDCK, lung cancer cells 549) and stimulating the growth of other normal cells (epithelial cells, renal tubular cells, keratinocytes, melanocytes), see Nippon Rinsho, 50, 1918 (1992).

A substance having diverse activities is anticipated to cause side effects in vivo and hence, it is desired to develop a substance capable of specifically stimulating the growth of hepatocytes.

In general, most of such substances (factors) are proteinaceous factors produced in a trace amount in vivo. In order to utilize such substances as reagents for studies, agents for diagnosis and therapeutic agents, it is thus required to produce these substances in a large scale and also for this reason, it is desired to clarify the structure of such substances.

DISCLOSURE OF INVENTION

The present inventors have made extensive studies with an attempt to obtain a novel gene coding for a hepatocyte growth factor from a rat liver and have succeeded in acquiring the novel gene coding for a hepatocyte growth factor from the rat residual liver after partial hepatectomy. Expression of this gene has resulted in successfully obtaining a novel parenchymal hepatocyte growth substance and successfully isolating and purifying the same substance from the rat residual liver after partial hepatectomy. Furthermore, the same gene has been successfully acquired from human liver. The present invention has thus been accomplished. That is, as a first aspect the present invention relates to:

a parenchymal hepatocyte growth substance which is a proteinaceous substance originating in a human or animal liver and having the following physico-chemical properties and physiological activities:
(1) an estimated molecular weight according to nonreductive SDS-PAGE of about 63,000 to about 69,000, an estimated molecular weight according to reductive SDS-PAGE of about 32,000 to about 36,000 and an estimated molecular weight according to gel filtration of about 60 to about 70 Kd;
(2) an activity of effecting the growth of parenchymal hepatocytes;
(3) said activity of effecting the growth of parenchymal hepatocytes being lost by a heat treatment at 95° C. for 5 minutes, a treatment with trypsin or a treatment with chymotrypsin;
(4) adsorption to an ion exchange resin; and,
(5) non-adsorption to heparin.

As a second aspect, the present invention relates to a gene coding for the parenchymal hepatocyte growth substance described above.

As a third aspect, the present invention relates to a process for producing a parenchymal hepatocyte growth substance which comprises transforming a host cell with an expression vector bearing the gene coding for the said parenchymal hepatocyte growth substance, culturing the resulting transformant and collecting the hepatic parenchymal cell growth substance from the culture medium.

As a fourth aspect, the present invention relates to as process for producing the parenchymal hepatocyte growth substance which comprises isolating the parenchymal hepatocyte growth substance from the homogenate of human or animal liver after partial hepatectomy, using an antibody to a partial peptide of the said parenchymal hepatocyte growth substance.

BRIEF DESCRIPTION OF DRAWINGS

FIG. 1 shows an amino acid sequence of the parenchymal hepatocyte growth substance originating in a human and animal liver and signal peptide (SEQ ID NOS:2 and 4).

FIG. 2 shows a nucleotide sequence of a gene coding for the parenchymal hepatocyte growth substance originating in a human and animal liver and signal peptide, namely, the former half of cDNA of the parenchymal hepatocyte growth substance (SEQ ID NOS:1 and 3).

FIG. 3 shows a nucleotide sequence of a gene coding for the parenchymal hepatocyte growth substance originating in a human and animal liver and signal peptide, namely, the latter half of CDNA of the parenchymal hepatocyte growth substance (SEQ ID NOS:1 and 3).

FIG. 4 shows a profile obtained by purification of the parenchymal hepatocyte growth substance originating in a rat liver through a Superose 12 column.

BEST MODE FOR CARRYING OUT THE INVENTION

Figure 5:
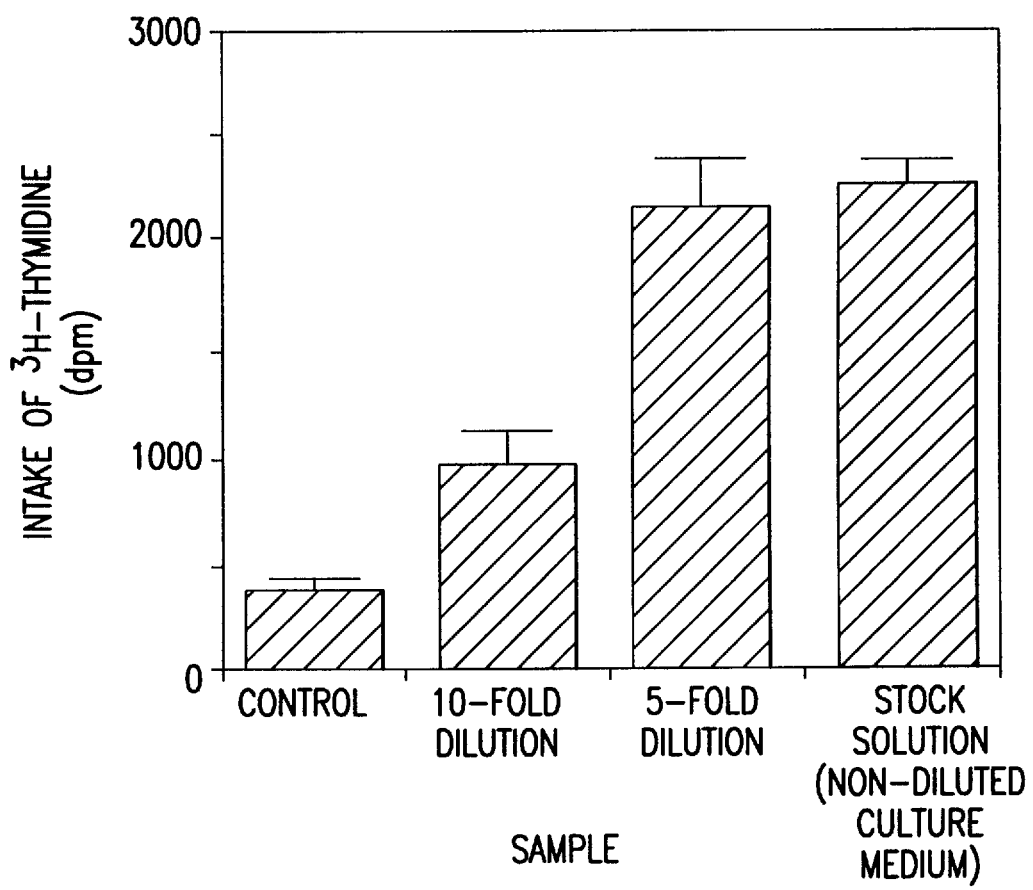
FIG. 5 shows the results obtained by evaluation of the growth activity of the rat liver-originating parenchymal hepatocyte growth substance for rat parenchymal hepatocyte in terms of incorporation of $^3$H-thymidine into DNA.

Hereinafter the present invention will be described in detail with respect to the steps of producing the parenchymal hepatocyte growth substance of the present invention and the gene coding for the substance, especially from rat and human livers.

Firstly, cDNA corresponding to the gene coding for the parenchymal hepatocyte growth substance that is considered to be specifically produced when rat liver is partially hepatectomized is surveyed and prepared by the following method.

(1) Construction of Liver cDNA Library of the Rat Residual Liver after Partial Hepatectomy It was first established by Higgins, G. M., et al that after partial hepatectomy, the rat liver is regenerated, see Arch. Pathol., 12, 186 (1981)/

After two-third of the liver is removed for partial hepatectomy, the peritoneum and skin are sutured. Again the rat is lapatectomized 12 hours after the liver removal when RNA synthesis increases and the residual liver is all removed. RNA can be extracted according to the guanidine hydrochloride method by Deeley, R. G., et al., J. Biol. Chem., 252, 8310 (1980).

Furthermore, the RNA can be subjected to oligo (Dt) cellulose column chromatography by a modification of the method by Amara, S. G., et al., J. Biol. Chem., 255, 2645 (1980), to prepare mRNA.

cDNA library can be constructed by synthesizing double-stranded cDNA from this MRNA and incorporating the double-stranded cDNA into, e.g., *E. coli* plasmid or phage.

It is assumed that this cDNA library would contain cDNA corresponding to the gene coding for the parenchymal hepatocyte growth substance expected to be specifically produced upon partial hepatectomy of a rat liver.

(2) Preparation of cDNA Probe in the Rat Residual Liver after partial Hepatectomy and cDNA Probe of Sham-Operated Rat Liver a) Preparation of cDNA probe in the rat residual liver after partial hepatectomy A part of the MRNA prepared by the oligo (Dt) cellulose column chromatography is used to synthesize double-stranded cDNA. Herein cDNA is isotope-labelled with [$\alpha$-$^{32}$P] dCTP according to the nick translation method, which is made cDNA probe of the rat residual liver after partial hepatectomy.

b) Preparation of cDNA Probe of Sham-Operated Rat Liver

After a rat is lapatectomized but no liver is removed, the peritoneum and skin are sutured. Again the rat is lapatectomized 12 hours after the operation and the liver is all removed. RNA is extracted according to the guanidine hydrochloride method and subjected to oligo (Dt) cellulose column chromatography to prepare mRNA. Using the mRNA as a template, double-stranded cDNA is synthesized while labelling with [$\alpha$-$^{32}$P] DCTP according to the nick translation method. The double-stranded cDNA is made CDNA probe of the sham-operated rat liver.

(3) Transfer of cDNA Library Clones onto a Nitrocellulose Membrane

Two nitrocellulose membrane sheets sterilized are previously put on an agar medium plate and all of the cDNA library clones obtained in (1) are transferred thereon by every two sheets under the same conditions. The clone-transferred nitrocellulose membranes are treated with an alkali and immobilized at 80° C.

(4) Hybridization by the cDNA Probe of the Residual Rat Liver after Partial Hepatectomy and by the CDNA Probe of Sham-Operated Rat Liver With respect to one membrane out of the two immobilized membranes of each clone in (3) above, hybridization is performed using the cDNA probe of the residual rat liver after partial hepatectomy, prepared in (2) a). For another membrane, hybridization is performed using the cDNA probe of sham-operated rat liver prepared in (2) b) above.

These membranes are overlaid on an X ray film, respectively and sensitized in an X ray film cassette for autoradiography. The clones sensitized with the cDNA probe from the rat residual liver after partial hepatectomy and those sensitized with the cDNA probe from the sham-operated rat liver are compared with the same clones to select only the clones that are more strongly sensitized with the cDNA probe from the residual liver than with the cDNA probe from the sham-operated liver. The thus obtained clones appear to contain cDNA clone coding for the parenchymal hepatocyte growth substance expected to be specifically produced by hepatectomy.

(5) Selection by Hybridization

Each of the selected clonal cDNAs is amplified by, e.g., PCR and the amplified cDNAS are immobilized or fixed onto a nitrocellulose membrane, respectively.

On the other hand, mRNAs are prepared from the rat residual liver after partial hepatectomy in a manner similar to (1) described above to prepare a mRNA solution having a high nucleotide concentration. The clonal CDNA-immobilized nitrocellulose membrane described above is immersed in the solution as a probe.

By this procedure, mRNA complementary to the clonal cDNA fixed onto each nitrocellulose membrane is adsorbed to the membrane. Thereafter the membrane is immersed in a solution having a low nucleotide concentration to obtain complementary MRNA.

(6) Expression of Protein

The MRNA solution obtained by hybridization selection is injected in a trace amount into *Xenopus laevis* oocyte. Incubation at 20° C. for 24 to 48 hours in a Barths' medium causes translation of the mRNA injected to express a protein. Where this protein is secretory, the protein can be produced in the medium.

(7) Evaluation of Hepatocyte Growth Activity

The hepatocyte growth activity of the protein expressed in (6) above is evaluated by the following method.

The parenchymal hepatocytes are separated from the rat liver to perform incubation of the primary liver cells. Upon the incubation, the culture broth containing the expressed protein obtained in (6) above is added thereto. In addition, $^3$H-thymidine is added to the medium and the $^3$H incorporated into the parenchymal hepatocytes after a definite period of time is counted with a liquid scintillation counter. By the change of $^3$H incorporated into the parenchymal hepatocytes, the hepatocyte growth activity can be evaluated.

mRNA capable of expressing the protein having a hepatocyte growth activity is selected and using the corresponding clonal cDNA, the following nucleotide sequence is analyzed so that the nucleotide sequence of the gene coding for the parenchymal hepatocyte growth substance can be determined.

(8) Analysis of Nucleotide sequence of the Gene cDNA Coding for the Parenchymal Hepatocyte Growth Substance In order to determine the nucleotide sequence of the gene corresponding to the mRNA capable of secreting the substance having a hepatocyte growth activity obtained in (7) described above, sequencing according to the dideoxy method or the like may be performed. The nucleotide sequence of the gene coding for the parenchymal hepatocyte growth substance is determined and based on the sequence determined, the amino acid sequence corresponding to the nucleotide sequence, namely, the amino acid sequence of the parenchymal hepatocyte growth substance can be speculated.

(9) Preparation of Anti-Partial Peptide Fragment Antibody of the Parenchymal Hepatocyte Growth Substance and Preparation of the Parenchymal Hepatocyte Growth Substance Based on the nucleotide sequence of the gene coding for the parenchymal hepatocyte growth substance, the corresponding amino acid sequence can be determined. Among them, a peptide corresponding to about 20 optional amino acid residues is synthesized and an animal such as rabbit is immunized with the peptide to prepare an antibody specific to the parenchymal hepatocyte growth substance. The antibody is bound to a column. Using the column, the parenchymal hepatocyte growth substance of the present invention can be isolated and extracted from the rat residual liver homogenate after partial hepatectomy.

(10) Preparation of the Parenchymal hepatocyte Growth Substance by Gene Expression The parenchymal hepatocyte growth substance-encoding cDNA obtained in (7) described above is transduced in an appropriate plasmid, e.g., pSVL (made by Pharmacia). After transforming, e.g., COS-7 cells, with this expression vector, the resulting transformant is cultured to express the parenchymal hepatocyte growth substance. The parenchymal hepatocyte growth substance of the present invention can be collected from the culture medium.

The gene coding for the parenchymal hepatocyte growth substance originating in a rat liver can be prepared by the steps described above and its nucleotide sequence can be determined. Furthermore, the parenchymal hepatocyte growth substance can be obtained by expressing of the gene. Alternatively, a partial peptide of the parenchymal hepatocyte growth substance is synthesized and by using an antibody to the peptide, the parenchymal hepatocyte growth substance can be isolated from the rat residual liver homogenate after partial hepatectomy.

Various mRNAS of animal cells or animal tissues such as human liver mRNA are commercially available and can be purchased from Clontech Co., Ltd., etc. to utilize them for the present invention.

Accordingly, cDNA library can be prepared by purchasing, e.g., human liver mRNA, synthesizing CDNA using the mRNA and incorporating this cDNA into a plasmid or phage.

From the resulting cDNA library cDNA coding for human liver-derived parenchymal hepatocyte growth substance can be acquired using as a probe the full length of or a part of cDNA coding for the parenchymal hepatocyte growth substance, which is obtained from the rat liver described above. Then, the nucleotide sequence of this cDNA can be determined according to the dideoxy method. The amino acid sequence can be deduced from the nucleotide sequence and an antibody can be prepared using as an antigen a peptide containing a part of the amino acid sequence; using the antibody, the parenchymal hepatocyte growth substance derived from human liver can be isolated and purified in a manner similar to above.

Alternatively, human liver cDNA can be transduced into, e.g., plasmid PSVL in a manner similar to above thereby to construct an expression vector and transform, e.g., COS-7 cells with the expression vector. Then, the resulting transformant is cultured and the human liver-derived parenchymal hepatocyte growth substance can also be obtained from the culture medium.

The thus obtained parenchymal hepatocyte growth substance of the present invention originating from a human or animal liver has the following properties.

(1) Molecular Weight

An estimated molecular weight according to nonreductive SDS-PAGE is about 63,000 to about 69,000, an estimated molecular weight according to reductive SDS-PAGE is about 32,000 to about 36,000 and an estimated molecular weight according to gel filtration is about 60 to about 70 Kd.

(2) Physiological Activity

The substance has an activity of effecting the growth of parenchymal hepatocytes.

(3) The activity of effecting the growth of parenchymal hepatocyte is lost by a heat treatment at 95° C. for 5 minutes, a treatment with trypsin or a treatment with chymotrypsin.

(4) The substance is adsorbed to an ion exchange resin such as DEAE Sepharose or Q-Sepharose.

(5) The substance is not adsorbed to heparin.

In addition, the parenchymal hepatocyte growth substance has the following characteristics.

The human liver-derived hepatic parenchymal cell growth substance has as its N-terminal amino acid sequence an amino acid sequence represented by formula (1) below (SEQ ID NO:5):

(N-terminus) Leu Glu Asp Cys Ala Gln Glu Gln Met Arg Leu Arg Ala Gln Val Arg Leu Leu Glu Thr Arg Val Lys Gln Gln Gln Val Lys Ile Lys (C-terminus)

wherein Leu, Glu, Asp, Cys, Ala, Gln, Met, Arg, Val, Thr, Lys and Ile wherein L, E, D, C, A, Q, M, R, V, L, T, K and I represent leucine, glutamic acid, aspartic acid, cysteine, alanine, glutamine, methionine, arginine, valine, leucine, threonine, lysine and isoleucine, respectively.

The full-length amino acid sequence of the human liver-derived parenchymal hepatocyte growth substance deduced from its CDNA nucleotide sequence appears to correspond to the amino acid sequence from 23 leucine to 312 isoleucine in the amino acid sequence shown in FIG. 1, lower column.

The rat liver-derived parenchymal hepatocyte growth substance has as its N-terminal amino acid sequence an amino acid sequence represented by formula (2) below (SEQ ID NO:6):

(N-terminus) Asp Glu Asn Cys Leu Gln Glu Gln Val Arg Leu Arg Ala Gln Val Arg Gln Leu Glu Thr Arg Val Lys Gln Gln Gln Val Val Ile Ala (C-terminus)

wherein Asp, Glu, cys, Leu, Gln, Val and Ile have the same significance as defined above and N represents asparagine.

The full-length amino acid sequence of the rat liver-derived parenchymal hepatocyte growth substance deduced from its cDNA nucleotide sequence appears to correspond to the amino acid sequence from 25 aspartic acid to 314 valine in the amino acid sequence shown in FIG. 1, upper column (SEQ ID NO:2).

An example of the gene coding for the aforesaid entire amino acid sequence of the human liver-derived parenchymal hepatocyte growth substance includes a gene having nucleotide sequence from codon CTC starting from 117 to codon ATT starting from 984 (corresponding to the portion shown by solid line with arrow in FIGS. 2 and 3) in the nucleotide sequences shown in FIGS. 2 and 3, lower column.

An example of the gene coding for the aforesaid entire amino acid sequence of the rat liver-derived parenchymal hepatocyte growth substance includes a gene having nucleotide sequence from codon GAT starting from 122 to codon GTT starting from 990 (corresponding to the portion shown by solid line with arrow in FIGS. 2 and 3) in the nucleotide sequences shown in FIGS. 2 and 3, upper column (SEQ ID NO:3-4).

These genes are determined according to the procedures for analysis of cDNA nucleotide sequence at step (8) in the process described above. Using these genes, the parenchymal hepatocyte growth substance of the present invention can be prepared according to the procedures shown in step (10) described above.

Hereinafter the present invention is described below in more detail by referring to Examples.

EXAMPLE 1

The following is an example for preparing the rat liver-derived parenchymal hepatocyte growth substance and the gene coding for the substance.

(1) Construction of Liver cDNA Library of the Rat Residual Liver after Partial Hepatectomy Sprague-Dawley male rat of 8 weeks age was lapatectomized in about 20–25 mm length from the xiphoid process along the center to withdraw the liver and cut off the right lateral lobe, left lateral lobe and the left median lobe. That is, about two-third of the liver was removed. Immediately thereafter, the peritoneum and skin were sutured. The rat was again lapatectomized 12 hours after the liver removal when RNA synthesis increased and the residual liver was all removed. To the liver removed was added 10-fold volume of 8M guanidine hydrochloride/20 Mm sodium acetate buffer (Ph 5.5). After thoroughly mixing with a homogenizer, the mixture was centrifuged at 18,000×g to obtain the supernatant as the sample solution. 5.7M cesium chloride was previously charged in a tube for ultracentrifugation and 8M guanidine hydrochloride/20 Mm sodium acetate (Ph 5.5) was overlaid thereon and, the sample solution was further overlaid thereon. Centrifugation was performed at 20° C. and 25 rpm for 20 hours.

By the above procedure, RNA was isolated as pellets. This RNA was dissolved in a suitable quantity of sterile water. An equal quantity of 0.4 Mm NaCl/20 Mm Tris hydrochloride buffer (Ph 7.4) was added to the solution and the mixture was poured onto an oligo (Dt) cellulose column which had been previously equilibrated with 0.2M NaCl/10 Mm Tris hydrochloride buffer (Ph 7.4). After rinsing with the same solution, elution was effected with 10 Mm Tris hydrochloride buffer/1 Mm EDTA (ethylenediamine tetraacetate) (Ph 7.4). The eluate was fractionated. With respect to a part of the fraction, absorbance was measured at 260 nm using a spectrophotometer to collect the elution peak. An equal quantity of 4M ammonium acetate was added to the elution peak collected followed by stirring. A 2-fold volume of ethanol was added to the stirred solution followed by thorough stirring. After allowing to stand at −20° C. for 3 hours, centrifugation was carried out at 4° C. for 5 minutes at 15,000 rpm and the resulting precipitates were mRNA to be used for the following experiment. According to the method of Land, H. (Nucl. Acids. Res., 9, 2251 (1981)), double-stranded CDNA was synthesized from the mRNA.

Next, double-stranded cDNA synthesized by the method of Maniatis, T. (Molecular Cloning, 249 (1982)) was inserted into E. coli plasmid pUC8. This recombinant DNA was transfected to E. coli HB101 for transformation. Approximately 68,000 clones were obtained as such transformed clones, which were made cDNA library of the rat residual liver after partial hepatectomy.

(2) Selection of Clone specifically expressed after partial Hepatectomy

The transformed clones in the cDNA library of the rat residual liver after partial hepatectomy were transferred onto two filters, respectively. The transfer onto the filters was conducted by overlaying the filters previously sterilized onto ampicillin-supplemented (50 μg/ml) LB agar medium (1% bacto-trypton, 0.5% yeast extract, 1% NaCl, pH 7.5) and transferring the transformed clones onto the two filters with a bamboo spit or tooth pick similarly sterilized. Incubation at 37° C. overnight resulted in proliferation of the E. coli clones on the filters to form colonies. The filters were treated with an alkali by a modification of the Grunstein, M. et al. method (Proc. Natl. Acad. Sci. USA, 72, 3691 (1975)) to fix the colonies onto the filters.

Using as a probe $[\alpha^{-32}p]$ dCTP-labeled cDNA of the rat residual liver after partial hepatectomy, hybridization was performed on one of the two filters fixed and on another filter, hybridization was performed using as a probe $[\alpha^{-32}p]$ dCTP-labeled cDNA of the sham-operated rat liver. The $[\alpha^{-32}p]$ dCTP-labeled cDNA of the rat residual liver after partial hepatectomy which was employed hereinabove was obtained by synthesizing double-stranded cDNA using a part of the mRNA obtained by oligo (dT) cellulose column chromatography in step (1) described above and labelling the cDNA with radioactive $[\alpha^{-32}p]$ dCTP according to the nick translation method. The $[\alpha^{-32}p]$ dCTP-labeled cDNA of the sham-operated rat liver was obtained by lapatectomizing a rat, suturing the peritoneum and the skin without removing the liver, again lapatectomizing the rat 12 hours after the operation to remove all of the residual liver, preparing mRNA in a manner similar to step (1) described above, and labelling the cDNA with radioactive $[\alpha^{-32}P]$ dCTP according to the nick translation method.

After the hybridization, each filter was washed at room temperature with 2×SSC (0.3M NaCl, 30 mM sodium citrate)/0.1% SDS (sodium dodecyl sulphate) and further with 0.1×SSC/0.1% SDS at 50° C. followed by drying.

The dried filters were overlaid on an X ray film, respectively, which was sensitized at −80° C. in an X ray film cassette for autoradiography. The clones sensitized with the cDNA probe from the rat residual liver after partial hepatectomy and those sensitized with the cDNA probe from the sham-operated rat liver were compared with the same clones to select only 40 clones that were more strongly sensitized with the cDNA probe from the residual liver than with the cDNA probe from the sham-operated liver.

(3) Evaluation of Hepatocyte Growth Activity

The aforesaid 40 clones cDNAs that appear to be specifically produced and amplified in the liver tissue in association with liver regeneration were amplified and adsorbed onto nitrocellulose filters, respectively, according to the method of Taniguchi et al. (Proc. Natl. Acad. Sci. USA, 77, 4003 (1980)).

The mRNA taken out of the residual liver 12 hours after partial hepatectomy was further adsorbed onto these filters in the presence of NaCl. After the filters were washed with NaCl, elution was performed with water to selectively obtain mRNA having a sequence complementary to the previously adsorbed clone cDNA. According to the method described in Colman, A., Transcription and translation, 271 (1984), this mRNA was condensed and injected in a trace amount into Xenopus laevis oocyte followed by incubation at 20° C. in a modified Barths' medium. After 48 hours, the culture medium was recovered and the growth activity of the parenchymal hepatocytes was evaluated as follows.

By circulation through the rat liver, the parenchymal hepatocytes were separated and cultured to provide for the evaluation. That is, Williams' E medium supplemented with 0.05% collagenase is circulated through the liver of Wistar strain male rat of 8 weeks age to separate hepatocytes. The separated cells are centrifuged at 50 g x for a minute and the supernatant was removed. The precipitated cells are gently suspended in Williams' E medium and the suspension was centrifuged several times in a similar manner. By this procedure, parenchymal hepatocytes can be obtained in a high purity. The cells are inoculated in a density of $2\times10^4$/$cm^2$ on a Petri dish previously coated with a collagen solution uniformly and then dried. Incubation is carried out at 37° C. in the presence of 5% carbon dioxide gas. The medium is exchanged with a fresh medium 3 to 6 hours after. At the same time, a specimen (the aforesaid culture medium obtained by culturing *Xenopus laevis* oocyte injected with mRNA) and is added to the medium in a definite amount. Twenty hours after, 0.1 $\mu$Ci of $^3$H-thymidine is added to the medium followed by incubation for further 6 to 20 hours. Then the $^3$H incorporated into the cells is counted. That is, the medium is removed and the cells are gently rinsed several times with PBS (phosphate buffer/physiological saline). The cells are further treated at 50° C. in the presence of 2N NaOH. The treated cells are stripped out of the Petri dish and dissolved. After neutralization, the amount of $^3$H is counted with a liquid scintillation counter. Where a substance having the growth activity is present in the specimen, the amount of $^3$H incorporated into the hepatocytes increases. For evaluation of the hepatocyte growth activity in such a manner, the parenchymal hepatocytes can be separated not only from the rat liver but also the liver of animals such as mouse, rabbit, etc. and provided for the evaluation.

According to the above method, the growth activity of the parenchymal hepatocytes was evaluated. Among 40 culture media (corresponding to the 40 clones) obtained by injecting the complementary mRNA, obtained in step (3) above using as templates the 40 clones cDNA obtained in step (2) above, into *Xenopus laevis* oocyte and culturing the oocyte, a highly potent parenchymal hepatocyte growth activity was noted in one medium (clone).

For control, comparison was made using the *Xenopus laevis* oocyte culture medium injected only with distilled water in a trace amount. The protein expressed only in the full-length mRNA-injected *Xenopus laevis* oocyte culture medium showed a molecular weight of about 60,000 to about 70,000 according to electro-phoresis (nonreductive SDS-PAGE).

(4) Determination of Nucleotide Sequence of the Gene cDNA Coding for the Parenchymal Hepatocyte Growth Substance The nucleotide sequence of clonal cDNA coding for the gene product showing a parenchymal hepatocyte growth activity, which was selected in step (3) above, was determined by the method of Nakamura et al. (Saibo Kogaku, 7, 712 (1988)). This clonal cDNA was considered to be deleted of the 5' end so that the following procedure was conducted to determine the site at the 5' end.

In order to newly prepare cDNA bearing the 5' end from the rat liver mRNA, firstly the residual liver was removed from the rat 12 hours after partial hepatectomy, in a manner similar to step (1) above, thereby to obtain mRNA. The mRNA obtained from the hemihepatectomized tissue was heated at 70° C. for 10 minutes and then quenched.

The oligonucleotide of 40 nucleotides complementary to the 40 nucleotides of the clonal cDNA at the 5' end obtained in step (3) above, which corresponds to the nucleotide sequence surrounded by square in FIG. 2 (SEQ ID NO:9):

(5' end) TGCCGTCAGATCGTCTC TGAATTACAGTCCATC-CTCCTCC (3' end)

was synthesized. Using this oligonucleotide as a primer and the aforesaid mRNA obtained from the hemi- hepatectomized tissue as a template, cDNA at the 5' end site was prepared. With respect to the thus obtained cDNA, the nucleotide sequence of the cDNA at the 5' end site which encodes the gene product was determined according to the method of Nakamura et al. (Saibo Kogaku, 7, 712 (1988)).

By the above procedure, the nucleotide sequence of the full-length cDNA coding for the rat liver-derived substance showing the parenchymal hepatocyte growth activity was revealed. The nucleotide sequence is shown in FIGS. 2 and 3, upper column (SEQ ID NO:1). The amino acid sequence of the rat liver-derived parenchymal hepatocyte growth substance shown in FIG. 1, upper column was deduced from the nucleotide sequence of FIGS. 2 and 3 (SEQ ID NO:2).

(5) Acquirement of Antibody to the Partial Peptide deduced from the Nucleotide Sequence and preparation of an Antibody Column Based on the nucleotide sequence of the gene determined in step (4) above, a peptide of hydrophilic portion was synthesized.

Three peptides of hydrophilic portion were prepared from the amino acid sequence shown in FIG. 1, upper column, which was deduced from the nucleotide sequence obtained in step (4) above. The amino acid sequences from 125 to 143, from 180 to 201 and from 236 to 256 were designated Peptides 1, 2 and 3, respectively. Each of three Japanese albino rabbits was boostered with Peptides 1 to 3, respectively, in a dose of 2 mg, one a week for 5 weeks.

As the result, antiserum obtained from Peptide 2 maintained the antibody titer even though it was diluted to 50,000-fold. From this serum the antibody was purified through a protein G column.

The purified antibody was bound to CNBr-activated Sepharose 4B to prepare an antibody column (R$\alpha$pep 200 IgG-Sepharose 4B column).

(6) Purification of the Parenchymal Hepatocyte Growth Substance

After the rat residual liver 24 hours after 70% partial hepatectomy was removed, the liver was thoroughly homogenized with a homogenizer. Centrifugation at 100,000×g at 4° C. for 30 minutes followed a treatment with heparin-cellurofine column. The non-adsorbed fraction was adsorbed to the antibody column prepared in step (5) above followed by elution with 0.15M ammonia –0.15M NaCl. The eluted fraction was concentrated. Gel filtration of the concentrate through a Superose 12 column gave a protein fraction reactive with the antibody at a molecular weight of about 65 kd. The purification profile through the Superose 12 column is shown in FIG. 4. With regard to the protein fraction thus obtained, the activity was determined according to the evaluation of hepatic parenchymal cell growth activity described in detail in step (3) above. The activity shown in FIG. 5 was appreciated.

Analysis of the amino acid sequence of the N-terminus of the purified parenchymal hepatocyte growth substance by Sequencing Analyzer (Applied Biosystems, Model 473A) revealed that the substance had the amino acid sequence shown by formula (2) below (SEQ ID NO:6).

(N-terminus) Asp Glu Asn cys Leu Gln Glu Gln Val Arg Leu Arg Ala Gln Val Arg Gln Leu Glu Thr Arg Val Lys Gln Gln Gln Val Val Ile Ala (C-terminus)

(7) Expression of Gene

In order to insert the gene coding for the parenchymal hepatocyte growth substance into COS-7 cells (Rikagaku Kenkyusho) originating from the kidney of African green monkey to produce a protein, the full-length cDNA coding for the parenchymal hepatocyte growth substance obtained in step (4) above, namely, cDNA having the nucleotide sequence at the upper column of the portion shown by dotted line with arrow in FIGS. 2 and 3, was inserted into plasmid pSVL (made by Pharmacia) bearing SV40 late promoter gene. Firstly this recombinant DNA was transfected to *E. coli* HB101 to perform DNA amplification. This recombinant DNA is made pSVLR. The thus obtained *E. coli* HB101 transfected with pSVLR was named *Escherichia coli* HB101-pR, which was deposited in the Life Science Research Institute of the Agency of Industrial Science and Technology of Japan on Nov. 17, 1992 and accepted under FERN P-13289. Then the strain was transferred to the international deposit and given an accession number of FERM BP-4594 on Mar. 3, 1994, pursuant to the Budapest Treaty.

Figure 6:
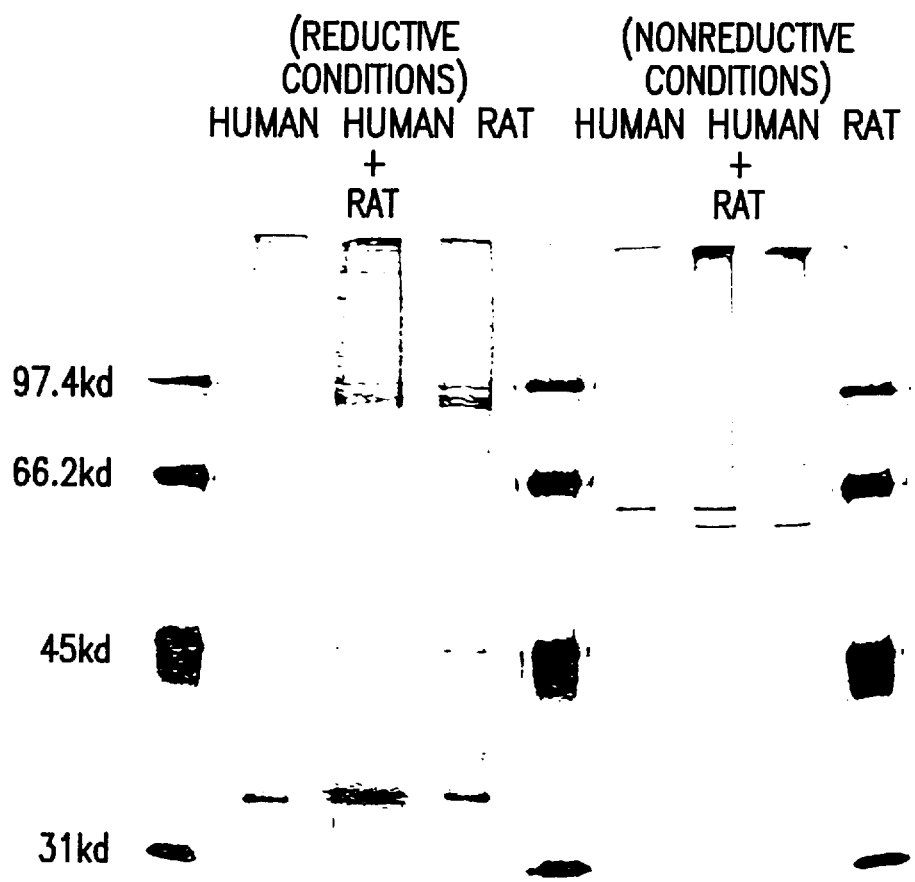
FIG. 6 shows the results of electrophoretic analysis of the parenchymal hepatocyte growth substance originating in rat and human livers.

The DNA was further transfected to COS-7 followed by incubation. DMEM was used as a medium and incubation was conducted at 37° C. for 4 to 6 days in the presence of 5% $CO_2$. The culture medium was recovered and subjected to electrophoresis by SDS-PAGE to obtain a band showing a molecular weight of about 63,000 to about 69,000 under nonreductive conditions and a molecular weight of about 32,000 to about 36,000 under reductive conditions. This was a band which was not present in the control (culture medium of the cells transfected only with pSVL). FIG. 6 indicates the results of the electrophoresis.

The culture medium described above was added to the primary culture medium of the hepatocytes and the hepatocyte growth activity was examined according to the method for determining the parenchymal hepatocyte growth activity shown in step (3) above. It was confirmed that the hepatocyte growth activity of the primary culture was present. No growth activity was observed in the culture medium of the cells transfected only with pSVL. It is thus assumed that this gene product would be the active substance.

The same gene as described above was inserted into vector-pCDL-SRα296 bearing HTLV-1.LTR gene, which was then transfected to Verots S-3 (Rikagaku Kenkyusho) originating from the kidney of African green monkey. Incubation was carried out in a similar manner. The culture medium was recovered and subjected to electro-phoresis by SDS-PAGE to give a band showing a molecular weight of about 63,000 to about 69,000 under nonreductive conditions and a molecular weight of about 32,000 to about 36,000 under reductive conditions. The culture medium described above was added to the primary culture medium of the hepatic cells and the hepatocyte growth activity was examined. It was confirmed that the hepatocyte growth activity of the primary culture was present.

Based on the findings on the molecular weight, the amino acid sequence shown in FIG. 1 and the amino acid sequence of the N-terminal portion described in step (6) above, it is considered that in the amino acid sequence shown in FIG. 1, upper column, the rat liver-derived parenchymal hepatocyte growth substance has the amino acid sequence from 25 aspartic acid to 314 valine (portion shown by the solid line with arrow in FIG. 1 (SEQ ID NO:2 ), takes a cyclic structure through two disulfide bonds (S—S bonds) within the molecule due to 5 cysteine residues contained in the amino acid sequence, and forms a homodimer in which two of such a molecule are bound to each other through the S—S bonds.

The protein expressed and recovered in step (7) above appears to be a protein in which signal peptide (amino acid sequence at the underlined portion in FIG. 1) corresponding to the amino acid sequence from 1 methionine to 24 glycine shown in FIG. 1, upper column is excised to form a dimer.

The nucleotide sequence of the gene coding for the rat liver-derived parenchymal hepatocyte growth substance is the nucleotide sequence (portion shown by the solid line with arrow in FIGS. 2 and 3) from codon GAT starting from 122 and to codon GTT starting from 990 in the nucleotide sequence shown in FIGS. 2 and 3, upper column (SEQ ID NO:1).

(8) Thermal Stability

The parenchymal hepatocyte growth substance obtained in steps (6) and (7) above was treated at 95° C. for 5 minutes. When the treated solution was added to the culture medium of the rat primary culture hepatocytes, no growth activity was exhibited on the hepatocytes.

(9) Stability against Trypsin and Chymotryosin

The parenchymal hepatocyte growth substance (5 μg/ml) obtained in steps (6) and (7) above was treated with trypsin (made by Sigma; 0.1 mg/ml) at 37° C. for 30 minutes. After trypsin was removed, the treated matter was added to the culture medium of the rat primary culture hepatocytes but no growth activity was exhibited on the hepatocytes.

When the substance was treated with chymotrypsin (made by Sigma; 0.1 mg/ml) at 37° C. for 30 minutes, the parenchymal hepatocyte growth activity was also lost.

(10) Column Characteristic P 1. Heparin-Sepharose

The culture medium, 1 liter, containing the parenchymal hepatocyte growth substance and produced by genetic recombination obtained in step (7) above was dialyzed to 20 mM phosphate buffer (pH 6.5)/0.5M NaCl for 16 hours and the dialysate was thoroughly equilibrated. Then the dialysate was poured through a heparin-Sepharose column (2×20 cm) equilibrated with the same buffer. After thoroughly washing with the same buffer, elution was performed with 20 mM phosphate buffer (pH 6.5)/2.0M NaCl. The parenchymal hepatocyte growth substance was found in the non-adsorbed fraction but absent in the eluted fraction. It was confirmed by electrophoresis (SDS-PAGE) and by the method for determining the parenchymal hepatocyte growth activity of the rat primary culture as to whether or not the substance was present. The results reveal that the parenchymal hepatocyte growth substance was not adsorbed to heparin-Sepharose.

2. CM Sepharose

The culture medium, 1 liter, containing the parenchymal hepatocyte growth substance and produced by genetic recombination obtained in step (7) above was dialyzed to 20 mM phosphate buffer (pH 6.5) for 16 hours. The dialysate was thoroughly equilibrated and then poured through a CM Sepharose column (2×20 cm) equilibrated with the same buffer. After thoroughly washing with the same buffer, elution was performed with 20 mM phosphate buffer (pH 6.5)/2.0M NaCl. The hepatic parenchymal cell growth substance was found in the non-adsorbed fraction but absent in the eluted fraction. It was confirmed by electrophoresis (SDS-PAGE) and by the method for determining the parenchymal hepatocyte growth activity of the rat primary culture as to whether or not the substance was present. The results reveal that the parenchymal hepatocyte growth substance was not adsorbed to CM Sepharose.

3. DEAE cellulose

The culture medium, 1 liter, containing the parenchymal hepatocyte growth substance and produced by genetic recombination obtained in step (7) above was dialyzed to 20 mM Tris hydrochloride buffer (pH 8.0) for 16 hours. The dialysate was thoroughly equilibrated and then poured through a DEAE Sepharose column (2×20 cm) equilibrated with the same buffer. After thoroughly washing with the same buffer, gradient elution was performed with 20 mM Tris hydrochloride buffer (pH 8.0)/2.0M NaCl. The parenchymal hepatocyte growth substance was found in a small amount in the non-adsorbed fraction and also eluted in the fraction of 0.5–0.8M NaCl. It was confirmed by electro-phoresis (SDS-PAGE) and by the method for determining the hepatic parenchymal cell growth activity of the rat primary culture as to whether or not the substance was present. The results reveal that the parenchymal hepatocyte growth substance was almost all adsorbed to DEAE Sepharose.

EXAMPLE 2

The parenchymal hepatocyte growth substance originating in a human liver is described below with reference to the following example.

(1) Selection of Human Liver cDNA

In order to obtain from a human liver cDNA having a high homology to cDNA coding for the rat liver-derived parenchymal hepatocyte growth substance, cDNA was prepared using human liver mRNA (made by Toyobo : Clontec). The cDNA was packaged in λgt11phage to construct a library.

From this library, cDNA having a high homology to the rat gene was obtained using as a probe cDNA of the rat liver-derived parenchymal hepatocyte growth substance obtained in Example 1, step (4), in which the 5' end site is deleted.

(2) Analysis of the Nucleotide Sequence of cDNA

In order to determine the nucleotide sequence of the gene cDNA obtained in step (1) above, the nucleotide sequence was determined according to the dideoxy method by a modification of the Nakamura et al. method (Saibo Kogaku, 7, 712 (1988)). The nucleotide sequence is shown in FIGS. 2 and 3, lower column (SEQ ID NO:3). The amino acid sequence deduced from the nucleotide sequence is shown in FIG. 1, lower column (SEQ ID NO:4).

(3) Expression of Gene

In order to insert the gene coding for the human liver-derived parenchymal hepatocyte growth substance into COS-7 cells (Rikagaku Kenkyusho) originating from the kidney of African green monkey to produce a protein, the full-length cDNA coding for the parenchymal hepatocyte growth substance obtained in step (1) above, namely, cDNA having the nucleotide sequence at the lower column of the portion shown by the dotted line with arrow in FIGS. 2 and 3, was inserted into plasmid pSVL (made by Pharmacia) bearing SV40 late promoter gene. Firstly this recombinant DNA was transfected to E. coli HB101 to perform DNA amplification. This recombinant DNA is made pSVLH. The thus obtained E. coli HB101 transfected with PSVLH was named Escherichia coli HB101-pH, which was deposited in the Life Science Research Institute of the Agency of Industrial Science and Technology of Japan on Nov. 17, 1992 and accepted under FERM P-13288. Then the strain was transferred to the international deposit and given an accession number of FERM BP-4593 on Mar. 3, 1994, pursuant to the Budapest Treaty.

The DNA was further transfected to COS-7 followed by incubation. DMEM was used as a medium and incubation was conducted at 37° C. for 4 to 6 days in the presence of 5% $CO_2$. The culture medium was recovered and subjected to electrophoresis by SDS-PAGE to obtain a band showing a molecular weight of about 63,000 to about 69,000 under nonreductive conditions and a molecular weight of about 32,000 to about 36,000 under reductive conditions. This was a band which was not present in the control (culture medium of the cells transfected only with PSVL). FIG. 6 indicates the results of the electrophoresis.

Figure 7:
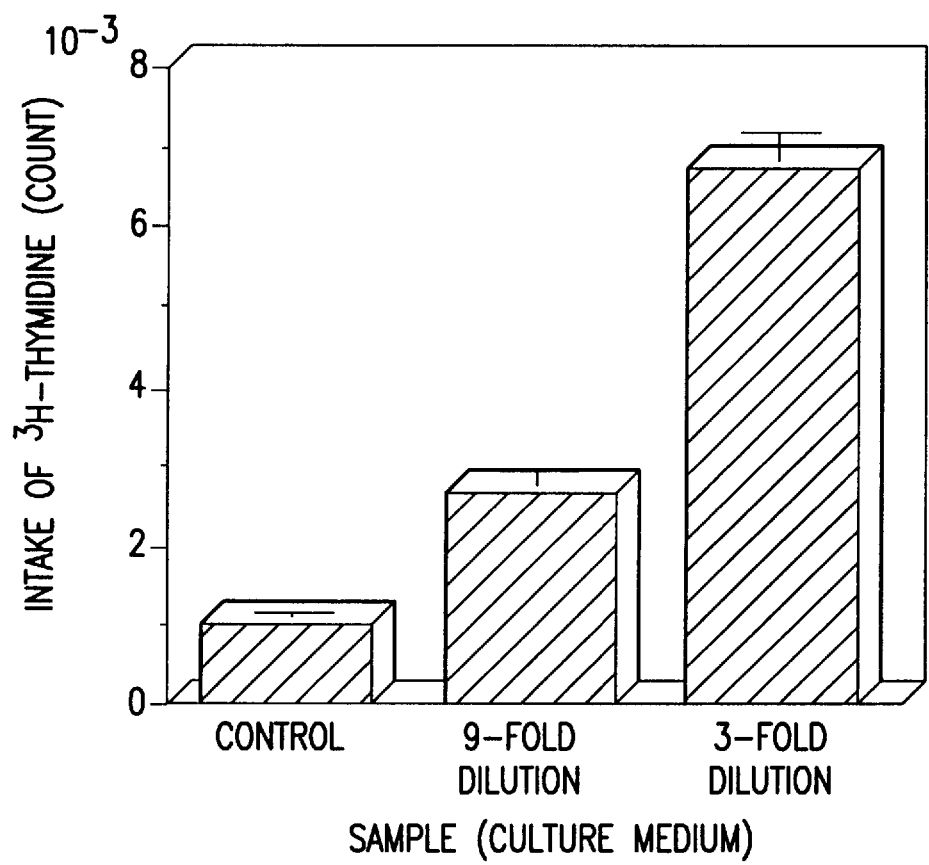
FIG. 7 shows the results obtained by evaluation of the growth activity of the human liver-originating parenchymal hepatocyte growth substance for rabbit parenchymal hepatocytes in terms of incorporation of $^3$H-thymidine into DNA.

The culture medium described above was added to the primary culture medium of the hepatocytes and the hepatocyte growth activity was examined according to the method for determining the parenchymal hepatocyte growth activity shown in Example 1, step (3). It was confirmed that the hepatocyte growth activity of the primary culture was present. The results of the activity evaluation are shown in FIG. 7. No growth activity was observed in the culture medium of the cells transfected only with pSVL. It is thus assumed that this gene product expressed would be the active substance.

The same gene as described above was inserted into vector-pCDL-SRα296 bearing HTLV-1.LTR gene, which was then transfected to Verots S-3 (Rikagaku Kenkyusho) originating from the kidney of African green monkey. Incubation was carried out in a similar manner. The culture medium was recovered and subjected to electro-phoresis by SDS-PAGE to give a band showing a molecular weight of about 63,000 to about 69,000 under nonreductive conditions and a molecular weight of about 32,000 to about 36,000 under reductive conditions. The culture medium described above was added to the primary culture medium of the hepatic cells and the hepatocyte growth activity was examined. It was confirmed that the hepatocyte growth activity of the primary culture was present.

The parenchymal hepatocyte growth substance was recovered and purified from the culture medium. Analysis of the amino acid sequence of the N-terminus of the purified substance by Sequencing Analyzer (Applied Biosystems, Model 473A) revealed that the substance had the amino acid sequence shown by formula (1) below as the N-terminal amino acid sequence (SEQ ID NO:5).

(N-terminus) Asp Glu Asn cys Leu Gln Glu Gln Val Arg Leu Arg
Ala Gin Val Arg Gln Leu Glu Thr Arg Val Lys gln Gln Val Val
Ile Ala (C-terminus)

Based on the foregoing findings, it is considered that in the amino acid sequence shown in FIG. 1, lower column, the human liver-derived parenchymal hepatocyte growth substance has the amino acid sequence from 23 leucine to 312 isoleucine (portion shown by the solid line with arrow in FIG. 1), takes a cyclic structure through two disulfide bonds within the molecule as in the rat liver-derived substance and forms a homodimer in which two of such a molecule are bound to each other through the disulfide bonds. The protein obtained by expression of the gene appears to be a protein in which signal peptide (amino acid sequence at the underlined portion in FIG. 1) corresponding to the amino acid sequence from 1 methionine to 22 alanine shown in FIG. 1, lower column is excised to form a dimer.

The nucleotide sequence of the gene coding for the human liver-derived parenchymal hepatocyte growth substance is the nucleotide sequence (portion shown by the solid line with arrow in FIGS. 2 and 3) from codon CTC starting from 117 and to codon ATT starting from 984 in the nucleotide sequence shown in FIGS. 2 and 3.

(4) Thermal Stability

The parenchymal hepatocyte growth substance obtained in step (3) above was treated at 95° C. for 5 minutes. When the treated solution was added to the culture medium of the rat primary culture hepatocytes, no growth activity was exhibited on the hepatocytes.

(5) Stability against Trypsin and Chymotrypsin

The human liver-derived parenchymal hepatocyte growth substance (5 μg/ml) obtained in step (3) above was treated with trypsin (made by Sigma; 0.1 mg/ml) at 37° C. for 30 minutes. After trypsin was removed, the treated matter was added to the culture medium of the rat primary culture hepatocytes but no growth activity was exhibited on the hepatocytes.

When the substance was treated with chymotrypsin (made by Sigma; 0.1 mg/ml) at 37° C. for 30 minutes, the parenchymal hepatocyte growth activity was also lost.

(6) Column Characteristic

1. Heparin-Sepharose

The culture medium, 1 liter, containing the parenchymal hepatocyte growth substance and produced by genetic recombination obtained in step (3) above was dialyzed to 20 mM phosphate buffer (pH 6.5)/0.5M NaCl for 16 hours and the dialysate was thoroughly equilibrated. Then the dialysate was poured through a heparin-Sepharose column (2×20 cm) equilibrated with the same buffer. After thoroughly washing with the same buffer, elution was performed with 20 mM phosphate buffer (pH 6.5)/2.0M NaCl. The parenchymal hepatocyte growth substance was found in the non-adsorbed fraction but absent in the eluted fraction. It was confirmed by electrophoresis (SDS-PAGE) and by the method for determining the parenchymal hepatocyte growth activity of the rat primary culture as to whether or not the substance was present. The results reveal that the parenchymal hepatocyte growth substance was not adsorbed to heparin-Sepharose.

2. CM Sepharose

The culture medium, 1 liter, containing the parenchymal hepatocyte growth substance and produced by genetic recombination obtained in step (3) above was dialyzed to 20 mM phosphate buffer (pH 6.5) for 16 hours. The dialysate was thoroughly equilibrated and then poured through a CM Sepharose column (2×20 cm) equilibrated with the same buffer. After thoroughly washing with the same buffer, elution was performed with 20 mM phosphate buffer (pH 6.5)/2.0M NaCl. The parenchymal hepatocyte growth substance was found in the non-adsorbed fraction but absent in the eluted fraction. It was confirmed by electrophoresis (SDS-PAGE) and by the method for determining the parenchymal hepatocyte growth activity of the rat primary culture as to whether or not the substance was present. The results reveal that the parenchymal hepatocyte growth substance was not adsorbed to CM Sepharose.

3. DEAE Cellulose

The culture medium, 1 liter, containing the parenchymal hepatocyte growth substance and produced by genetic recombination obtained in step (3) above was dialyzed to 20 mM Tris hydrochloride buffer (pH 8.0) for 16 hours. The dialysate was thoroughly equilibrated and then poured through a DEAE Sepharose column (2×20 cm) equilibrated with the same buffer. After thoroughly washing with the same buffer, gradient elution was performed with 20 mM Tris hydrochloride buffer (pH 8.0)/2.0M NaCl. The parenchymal hepatocyte growth substance was found in a small amount in the non-adsorbed fraction and also eluted in the fraction of 0.5–0.8M NaCl. It was confirmed by electrophoresis (SDS-PAGE) and by the method for determining the parenchymal hepatocyte growth activity of the rat primary culture as to whether or not the substance was present. The results reveal that the parenchymal hepatocyte growth substance was almost all adsorbed to DEAE Sepharose.

Industrial Applicability

According to the present invention, novel parenchymal hepatocyte growth substance originating in a human or animal liver can be obtained and this substance possesses an activity of extracellularly proliferating parenchymal hepatocytes. According to the present invention, there is also provided a gene coding for the parenchymal hepatocyte growth substance and using the gene, the parenchymal hepatocyte growth substance can be mass-produced by genetic recombination technique.

Therefore, the present invention has an extreme significance in providing a route for development of a new therapeutic agent for liver diseases and a new agent for clinical diagnosis for hepatitis and hepatic function test.

We claim:

1. An isolated and purified parenchymal hepatocyte growth factor substance which is naturally produced in a non-nalion liver and has the following physicochemical properties and physiological activities:

(1) an estimated molecular weight according to nonreductive SDS-PAGE of about 63,000 to about 69,000, an estimated molecular weight according to reductive SDS-PAGE of about 32,000 to about 36,000 and an estimated molecular weight according to gel filtration of about 60 to about 70 Kd;

(2) an activity of effecting the growth of parenchymal hepatocytes;

(3) said activity of effecting the growth of parenchymal hepatocytes being lost by a heat treatment at 95° C. for 5 minutes, a treatment with trypsin or a treatment with chymotrypsin;

(4) adsorption to DEAE Sepharose resin at pH 8.0 in 20 mM Tris hydrochloride buffer; and (5) non-adsorption to heparin.

2. A parenchymal hepatocyte growth factor to claim 1, having an N-terminal amino acid sequence of SEQ ID NO:5.

3. A parenchymal hepatocyte growth factor according to claim 1, having an N-terminal amino acid sequence of SEQ ID NO:6.

4. A parenchymal hepatocyte growth factor according to claim 2, wherein said factor has an amino acid sequence from 23 leucine to 312 isoleucine in the amino acid sequence of SEQ ID NO:4.

5. A parenchymal hepatocyte growth factor according to claim 3, wherein said factor has an amino acid sequence from 25 aspartic acid to 314 valine in the amino acid sequence of SEQ ID NO:2.

6. An isolated DNA coding for a parenchymal hepatocyte growth factor having an amino acid sequence from 23 leucine to 312 isoleucine in the amino acid sequence of SEQ ID NO:4.

7. An isolated DNA coding for a parenchymal hepatocyte growth substance having an amino acid sequence from 25 aspartic acid to 314 valine in the amino acid sequence of SEQ ID NO:2.

8. A process for producing a parenchymal hepatocyte growth factor according to claim 1, which comprises transforming a host cell with an expression vector comprising a DNA coding for a parenchymal hepatocyte growth factor having an amino acid sequence from 23 leucine to 312 isoleucine in the amino acid sequence of SEQ ID NO:4, culturing the resulting transformant and recovering the parenchymal hepatocyte growth factor from the culture medium.

9. A process for producing a parenchymal hepatocyte growth factor according to claim 1, which comprises transforming a host cell with an expression vector comprising a DNA coding for a parenchymal hepatocyte growth factor having an amino acid sequence from 25 aspartic acid to 314 valine in the amino acid sequence of SEQ ID NO:2, culturing the resulting transformant and recovering the parenchymal hepatocyte growth factor from the culture medium.

10. A process for isolating a parenchymal hepatocyte growth factor according to claim 1, comprising:

contacting an antibody to a peptide having the sequence of amino acids 180 to 201 of SEQ ID NO:2 with a homogenate of a mammalian liver after a partial hepatectomy of said liver to form an antibody-parenchymal hepatocyte growth factor complex; and isolating said parenchymal hepatocyte growth factor from said complex.

11. The process according to claim 10, wherein said antibody is bound to a column.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1101 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 48..989

( i x ) FEATURE:
        ( A ) NAME/KEY: sig_peptide
        ( B ) LOCATION: 48..119

( x i ) SEQUENCE DESCRIPTION: SEQ ID NO:1:

```
GACCCAGCCT AGCTGAGTAC TGATTCATTT TGATGTGAGT GGGAAGA ATG GGG GAG        56
                                                    Met Gly Glu
                                                      1

ATT CGC AGC TTT GTC CTC ATC ACT GTT GCT CTG ATT CTG GGC AAG GAG       104
Ile Arg Ser Phe Val Leu Ile Thr Val Ala Leu Ile Leu Gly Lys Glu
      5                  10                 15
```

```
AGC TGG GTC CTC GGA GAT GAG AAC TGT TTG CAG GAG CAG GTC AGG CTC      152
Ser Trp Val Leu Gly Asp Glu Asn Cys Leu Gln Glu Gln Val Arg Leu
 20              25              30              35

AGG GCT CAG GTG CGC CAG CTT GAG ACC CGG GTC AAA CAA CAA CAG GTG      200
Arg Ala Gln Val Arg Gln Leu Glu Thr Arg Val Lys Gln Gln Gln Val
                 40              45              50

GTG ATT GCA CAG CTC TTG CAC GAG AAG GAG GTC CAG TTC CTG GAT AGA      248
Val Ile Ala Gln Leu Leu His Glu Lys Glu Val Gln Phe Leu Asp Arg
             55              60              65

GGA CAG GAG GAC AGC TTC ATT GAC CTT GGA GGC AAG AGG CAT TAC GCA      296
Gly Gln Glu Asp Ser Phe Ile Asp Leu Gly Gly Lys Arg His Tyr Ala
         70              75              80

GAT TGT TCA GAG ATT TAC AAT GAT GGA TTT AAA CAT AGT GGG TTT TAC      344
Asp Cys Ser Glu Ile Tyr Asn Asp Gly Phe Lys His Ser Gly Phe Tyr
     85              90              95

AAA ATC AAA CCT CTT CAG AGT CTG GCA GAA TTC TCT GTT TAT TGT GAT      392
Lys Ile Lys Pro Leu Gln Ser Leu Ala Glu Phe Ser Val Tyr Cys Asp
100             105             110                         115

ATG TCT GAT GGA GGA GGA TGG ACT GTA ATT CAG AGA CGA TCT GAC GGC      440
Met Ser Asp Gly Gly Gly Trp Thr Val Ile Gln Arg Arg Ser Asp Gly
                 120             125             130

AGT GAG AAC TTT AAC AGG GGT TGG AAC GAC TAT GAA AAT GGC TTT GGA      488
Ser Glu Asn Phe Asn Arg Gly Trp Asn Asp Tyr Glu Asn Gly Phe Gly
             135             140             145

AAC TTT GTC CAA AGC AAT GGT GAA TAC TGG CTG GGT AAC AAA AAC ATT      536
Asn Phe Val Gln Ser Asn Gly Glu Tyr Trp Leu Gly Asn Lys Asn Ile
         150             155             160

AAC TTG CTG ACT ATG CAA GGA GAC TAC ACT TTA AAA ATC GAC CTG ACA      584
Asn Leu Leu Thr Met Gln Gly Asp Tyr Thr Leu Lys Ile Asp Leu Thr
     165             170             175

GAC TTT GAG AAA AAC AGC CGC TTC GCA CAA TAC GAA AAA TTT AAA GTT      632
Asp Phe Glu Lys Asn Ser Arg Phe Ala Gln Tyr Glu Lys Phe Lys Val
180             185             190                         195

GGC GAT GAA AAG TCT TTT TAC GAA CTG AAT ATT GGA GAA TAT TCT GGC      680
Gly Asp Glu Lys Ser Phe Tyr Glu Leu Asn Ile Gly Glu Tyr Ser Gly
                 200             205             210

ACC GCC GGA GAC TCC CTG TCG GGA ACA TTT CAC CCT GAA GTG CAG TGG      728
Thr Ala Gly Asp Ser Leu Ser Gly Thr Phe His Pro Glu Val Gln Trp
             215             220             225

TGG GCT AGT CAC CAA ACA ATG AAG TTC AGC ACA CGG GAC AGA GAC AAC      776
Trp Ala Ser His Gln Thr Met Lys Phe Ser Thr Arg Asp Arg Asp Asn
         230             235             240

GAC AAC TAC AAC GGG AAC TGT GCT GAG GAG GAA CAG TCT GGC TGG TGG      824
Asp Asn Tyr Asn Gly Asn Cys Ala Glu Glu Glu Gln Ser Gly Trp Trp
     245             250             255

TTT AAC AGG TGT CAC TCT GCA AAC CTG AAC GGC GTG TAC TAC CAA GGT      872
Phe Asn Arg Cys His Ser Ala Asn Leu Asn Gly Val Tyr Tyr Gln Gly
260             265             270                         275

CCC TAC AGA GCA GAA ACC GAT AAT GGT GTT GTC TGG TAC ACC TGG CGT      920
Pro Tyr Arg Ala Glu Thr Asp Asn Gly Val Val Trp Tyr Thr Trp Arg
                 280             285             290

GGG TGG TGG TAT TCC TTG AAA TCT GTG GTT ATG AAA ATT AGG CCC AGT      968
Gly Trp Trp Tyr Ser Leu Lys Ser Val Val Met Lys Ile Arg Pro Ser
             295             300             305

GAT TTT ATT CCA AAT ATC GTT TAGTTGTCCC ATTGGGATCT GCTTTCTGTG        1019
Asp Phe Ile Pro Asn Ile Val
         310

ATTCATCTTG GTTTTTAAAT GTTTGAAAAA AATATACAAT TCTGAATAAT ACACTCGTGG   1079

CGATGGTGAA AAAAAAAAAA AA                                            1101
```

( 2 ) INFORMATION FOR SEQ ID NO:2:

( i ) SEQUENCE CHARACTERISTICS:
        ( A ) LENGTH: 314 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Glu Ile Arg Ser Phe Val Leu Ile Thr Val Ala Leu Ile Leu
 1               5                  10                  15
Gly Lys Glu Ser Trp Val Leu Gly Asp Glu Asn Cys Leu Gln Glu Gln
             20                  25                  30
Val Arg Leu Arg Ala Gln Val Arg Gln Leu Glu Thr Arg Val Lys Gln
                 35                  40                  45
Gln Gln Val Val Ile Ala Gln Leu Leu His Glu Lys Glu Val Gln Phe
         50                  55                  60
Leu Asp Arg Gly Gln Glu Asp Ser Phe Ile Asp Leu Gly Gly Lys Arg
 65                  70                  75                  80
His Tyr Ala Asp Cys Ser Glu Ile Tyr Asn Asp Gly Phe Lys His Ser
                 85                  90                  95
Gly Phe Tyr Lys Ile Lys Pro Leu Gln Ser Leu Ala Glu Phe Ser Val
                100                 105                 110
Tyr Cys Asp Met Ser Asp Gly Gly Gly Trp Thr Val Ile Gln Arg Arg
             115                 120                 125
Ser Asp Gly Ser Glu Asn Phe Asn Arg Gly Trp Asn Asp Tyr Glu Asn
     130                 135                 140
Gly Phe Gly Asn Phe Val Gln Ser Asn Gly Glu Tyr Trp Leu Gly Asn
145                 150                 155                 160
Lys Asn Ile Asn Leu Leu Thr Met Gln Gly Asp Tyr Thr Leu Lys Ile
                 165                 170                 175
Asp Leu Thr Asp Phe Glu Lys Asn Ser Arg Phe Ala Gln Tyr Glu Lys
             180                 185                 190
Phe Lys Val Gly Asp Glu Lys Ser Phe Tyr Glu Leu Asn Ile Gly Glu
         195                 200                 205
Tyr Ser Gly Thr Ala Gly Asp Ser Leu Ser Gly Thr Phe His Pro Glu
    210                 215                 220
Val Gln Trp Trp Ala Ser His Gln Thr Met Lys Phe Ser Thr Arg Asp
225                 230                 235                 240
Arg Asp Asn Asp Asn Tyr Asn Gly Asn Cys Ala Glu Glu Glu Gln Ser
                 245                 250                 255
Gly Trp Trp Phe Asn Arg Cys His Ser Ala Asn Leu Asn Gly Val Tyr
             260                 265                 270
Tyr Gln Gly Pro Tyr Arg Ala Glu Thr Asp Asn Gly Val Val Trp Tyr
         275                 280                 285
Thr Trp Arg Gly Trp Trp Tyr Ser Leu Lys Ser Val Val Met Lys Ile
    290                 295                 300
Arg Pro Ser Asp Phe Ile Pro Asn Ile Val
305                 310
```

( 2 ) INFORMATION FOR SEQ ID NO:3:

( i ) SEQUENCE CHARACTERISTICS:
        ( A ) LENGTH: 1093 base pairs
        ( B ) TYPE: nucleic acid
        ( C ) STRANDEDNESS: single ( D ) TOPOLOGY: linear ( i i ) MOLECULE TYPE: cDNA ( i x ) FEATURE:
    ( A ) NAME/KEY: CDS
    ( B ) LOCATION: 51..986

( i x ) FEATURE:
    ( A ) NAME/KEY: sig_peptide
    ( B ) LOCATION: 51..116

( x i ) SEQUENCE DESCRIPTION: SEQ ID NO:3:

```
TGAGCTGGGT CTCTGACTCA CTTCTGACTT TAGTTTTTTC AAGGGGGAAC ATG GCA         56
                                                         Met Ala
                                                         1

AAG GTG TTC AGT TTC ATC CTT GTT ACC ACC GCT CTG ATA ATG GGC AGG        104
Lys Val Phe Ser Phe Ile Leu Val Thr Thr Ala Leu Ile Met Gly Arg
          5                   10                  15

GAA ATT TCG GCG CTC GAG GAC TGT GCC CAG GAG CAG ATG CGG CTC AGA        152
Glu Ile Ser Ala Leu Glu Asp Cys Ala Gln Glu Gln Met Arg Leu Arg
     20                  25                  30

GCC CAG GTG CGC CTG CTT GAG ACC CGG GTC AAA CAG CAA CAG GTC AAG        200
Ala Gln Val Arg Leu Leu Glu Thr Arg Val Lys Gln Gln Gln Val Lys
 35                  40                  45                   50

ATC AAG CAG CTT TTG CAG GAG AAT GAA GTC CAG TTC CTT GAT AAA GGA        248
Ile Lys Gln Leu Leu Gln Glu Asn Glu Val Gln Phe Leu Asp Lys Gly
                 55                  60                  65

GAT GAG AAT ACT GTC GTT GAT CTT GGA AGC AAG AGG CAG TAT GCA GAT        296
Asp Glu Asn Thr Val Val Asp Leu Gly Ser Lys Arg Gln Tyr Ala Asp
             70                  75                  80

TGT TCA GAG ATT TTC AAT GAT GGG TAT AAG CTC AGT GGA TTT TAC AAA        344
Cys Ser Glu Ile Phe Asn Asp Gly Tyr Lys Leu Ser Gly Phe Tyr Lys
         85                  90                  95

ATC AAA CCT CTC CAG AGC CCA GCA GAA TTT TCT GTT TAT TGT GAC ATG        392
Ile Lys Pro Leu Gln Ser Pro Ala Glu Phe Ser Val Tyr Cys Asp Met
    100                 105                 110

TCC GAT GGA GGA GGA TGG ACT GTA ATT CAG AGA CGA TCT GAT GGC AGT        440
Ser Asp Gly Gly Gly Trp Thr Val Ile Gln Arg Arg Ser Asp Gly Ser
115                 120                 125                 130

GAA AAC TTT AAC AGA GGA TGG AAA GAC TAT GAA AAT GGC TTT GGA AAT        488
Glu Asn Phe Asn Arg Gly Trp Lys Asp Tyr Glu Asn Gly Phe Gly Asn
                135                 140                 145

TTT GTC CAA AAA CAT GGT GAA TAT TGG CTG GGC AAT AAA AAT CTT CAC        536
Phe Val Gln Lys His Gly Glu Tyr Trp Leu Gly Asn Lys Asn Leu His
            150                 155                 160

TTC TTG ACC ACT CAA GAA GAC TAC ACT TTA AAA ATC GAC CTT GCA GAT        584
Phe Leu Thr Thr Gln Glu Asp Tyr Thr Leu Lys Ile Asp Leu Ala Asp
        165                 170                 175

TTT GAA AAA AAT AGC CGT TAT GCA CAA TAT AAG AAT TTC AAA GTT GGA        632
Phe Glu Lys Asn Ser Arg Tyr Ala Gln Tyr Lys Asn Phe Lys Val Gly
    180                 185                 190

GAT GAA AAG AAT TTC TAC GAG TTG AAT ATT GGG GAA TAT TCT GGA ACA        680
Asp Glu Lys Asn Phe Tyr Glu Leu Asn Ile Gly Glu Tyr Ser Gly Thr
195                 200                 205                 210

GCT GGA GAT TCC CTT GCG GGG AAT TTT CAT CCT GAG GTG CAG TGG TGG        728
Ala Gly Asp Ser Leu Ala Gly Asn Phe His Pro Glu Val Gln Trp Trp
                215                 220                 225

GCT AGT CAC CAA AGA ATG AAA TTC AGC ACG TGG GAC AGA GAT CAT GAC        776
Ala Ser His Gln Arg Met Lys Phe Ser Thr Trp Asp Arg Asp His Asp
            230                 235                 240

AAC TAT GAA GGG AAC TGC GCA GAA GAA GAT CAG TCT GGC TGG TGG TTT        824
Asn Tyr Glu Gly Asn Cys Ala Glu Glu Asp Gln Ser Gly Trp Trp Phe
```

```
                    2 4 5                           2 5 0                              2 5 5
AAC  AGG  TGT  CAC  TCT  GCA  AAC  CTG  AAT  GGT  GTA  TAC  TAC  AGC  GGC  CCC         872
Asn  Arg  Cys  His  Ser  Ala  Asn  Leu  Asn  Gly  Val  Tyr  Tyr  Ser  Gly  Pro
     260                      265                     270

TAC  ACG  GCT  AAA  ACA  GAC  AAT  GGG  ATT  GTC  TGG  TAC  ACC  TGG  CAT  GGG         920
Tyr  Thr  Ala  Lys  Thr  Asp  Asn  Gly  Ile  Val  Trp  Tyr  Thr  Trp  His  Gly
275                      280                     285                          290

TGG  TGG  TAT  TCT  CTG  AAA  TCT  GTG  GTT  ATG  AAA  ATT  AGG  CCA  AAT  GAT         968
Trp  Trp  Tyr  Ser  Leu  Lys  Ser  Val  Val  Met  Lys  Ile  Arg  Pro  Asn  Asp
               295                     300                     305

TTT  ATT  CCA  AAT  GTA  ATT  TAATTGCTGC  TGTTGGGCTT  TCGTTTCTGC                      1016
Phe  Ile  Pro  Asn  Val  Ile
               310

AATTCAGCTT  TGTTTAAAGT  GATTTGAAAA  ATACTCATTC  TGAACATATC  CAGCGCAATC                1076

ATGATAACTG  TTGTGAG                                                                   1093
```

( 2 ) INFORMATION FOR SEQ ID NO:4:

( i ) SEQUENCE CHARACTERISTICS:
        ( A ) LENGTH: 312 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Lys  Val  Phe  Ser  Phe  Ile  Leu  Val  Thr  Thr  Ala  Leu  Ile  Met
 1                        5                    10                      15

Gly  Arg  Glu  Ile  Ser  Ala  Leu  Glu  Asp  Cys  Ala  Gln  Glu  Gln  Met  Arg
               20                      25                     30

Leu  Arg  Ala  Gln  Val  Arg  Leu  Leu  Glu  Thr  Arg  Val  Lys  Gln  Gln  Gln
          35                      40                     45

Val  Lys  Ile  Lys  Gln  Leu  Leu  Gln  Glu  Asn  Glu  Val  Gln  Phe  Leu  Asp
     50                      55                     60

Lys  Gly  Asp  Glu  Asn  Thr  Val  Val  Asp  Leu  Gly  Ser  Lys  Arg  Gln  Tyr
 65                      70                     75                          80

Ala  Asp  Cys  Ser  Glu  Ile  Phe  Asn  Asp  Gly  Tyr  Lys  Leu  Ser  Gly  Phe
                    85                      90                          95

Tyr  Lys  Ile  Lys  Pro  Leu  Gln  Ser  Pro  Ala  Glu  Phe  Ser  Val  Tyr  Cys
               100                     105                    110

Asp  Met  Ser  Asp  Gly  Gly  Gly  Trp  Thr  Val  Ile  Gln  Arg  Arg  Ser  Asp
               115                     120                    125

Gly  Ser  Glu  Asn  Phe  Asn  Arg  Gly  Trp  Lys  Asp  Tyr  Glu  Asn  Gly  Phe
     130                     135                    140

Gly  Asn  Phe  Val  Gln  Lys  His  Gly  Glu  Tyr  Trp  Leu  Gly  Asn  Lys  Asn
145                     150                     155                         160

Leu  His  Phe  Leu  Thr  Thr  Gln  Glu  Asp  Tyr  Thr  Leu  Lys  Ile  Asp  Leu
               165                     170                    175

Ala  Asp  Phe  Glu  Lys  Asn  Ser  Arg  Tyr  Ala  Gln  Tyr  Lys  Asn  Phe  Lys
               180                     185                    190

Val  Gly  Asp  Glu  Lys  Asn  Phe  Tyr  Glu  Leu  Asn  Ile  Gly  Glu  Tyr  Ser
               195                     200                    205

Gly  Thr  Ala  Gly  Asp  Ser  Leu  Ala  Gly  Asn  Phe  His  Pro  Glu  Val  Gln
     210                     215                    220

Trp  Trp  Ala  Ser  His  Gln  Arg  Met  Lys  Phe  Ser  Thr  Trp  Asp  Arg  Asp
225                     230                     235                         240

His  Asp  Asn  Tyr  Glu  Gly  Asn  Cys  Ala  Glu  Glu  Asp  Gln  Ser  Gly  Trp
```

-continued

```
                                  245                                    250                                    255
Trp  Phe  Asn  Arg  Cys  His  Ser  Ala  Asn  Leu  Asn  Gly  Val  Tyr  Tyr  Ser
               260                      265                     270

Gly  Pro  Tyr  Thr  Ala  Lys  Thr  Asp  Asn  Gly  Ile  Val  Trp  Tyr  Thr  Trp
               275                      280                     285

His  Gly  Trp  Trp  Tyr  Ser  Leu  Lys  Ser  Val  Val  Met  Lys  Ile  Arg  Pro
               290                      295                     300

Asn  Asp  Phe  Ile  Pro  Asn  Val  Ile
305                      310
```

(2) INFORMATION FOR SEQ ID NO:5:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Leu  Glu  Asp  Cys  Ala  Gln  Glu  Gln  Met  Arg  Leu  Arg  Ala  Gln  Val  Arg
1                   5                        10                       15

Leu  Leu  Glu  Thr  Arg  Val  Lys  Gln  Gln  Val  Lys  Ile  Lys
               20                      25                      30
```

(2) INFORMATION FOR SEQ ID NO:6:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Asp  Glu  Asn  Cys  Leu  Gln  Glu  Gln  Val  Arg  Leu  Arg  Ala  Gln  Val  Arg
1                   5                        10                       15

Gln  Leu  Glu  Thr  Arg  Val  Lys  Gln  Gln  Gln  Val  Val  Ile  Ala
               20                      25                      30
```

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

TGCCGTCAGA TCGTCTCTGA ATTACAGTCC ATCCTCCTCC 40